US009453816B2

(12) United States Patent
Morimoto

(10) Patent No.: US 9,453,816 B2
(45) Date of Patent: Sep. 27, 2016

(54) DIFFERENTIAL TRANSFORMER TYPE MAGNETIC SENSOR AND IMAGE FORMING APPARATUS

(71) Applicant: KYOCERA Document Solutions Inc., Osaka (JP)

(72) Inventor: Masashi Morimoto, Osaka (JP)

(73) Assignee: KYOCERA DOCUMENT SOLUTIONS INC., Osaka (JP)

( * ) Notice: Subject to any disclaimer, the term of this patent is extended or adjusted under 35 U.S.C. 154(b) by 512 days.

(21) Appl. No.: 14/050,724

(22) Filed: Oct. 10, 2013

(65) Prior Publication Data

US 2014/0103910 A1   Apr. 17, 2014

(30) Foreign Application Priority Data

Oct. 15, 2012 (JP) .................... 2012-227992

(51) Int. Cl.
G01R 33/02 (2006.01)
G01N 27/74 (2006.01)
G01R 33/04 (2006.01)
G03G 15/08 (2006.01)

(52) U.S. Cl.
CPC .............. *G01N 27/74* (2013.01); *G01R 33/04* (2013.01); *G03G 15/086* (2013.01); *G03G 15/0829* (2013.01); *G03G 15/0831* (2013.01); *G03G 15/0853* (2013.01); *G03G 15/0856* (2013.01)

(58) Field of Classification Search
CPC .. G01N 27/74; G01R 33/04; G03G 15/0829; G03G 15/0831; G03G 15/0853; G03G 15/0856; G03G 15/086
See application file for complete search history.

(56) References Cited

U.S. PATENT DOCUMENTS 4,786,869 A * 11/1988 Kanai ................. G03G 15/086
                                                    118/712
4,942,431 A *  7/1990 Tada .................. G03G 15/0849
                                                    399/260

(Continued)

FOREIGN PATENT DOCUMENTS

GB    2 340 251 A    2/2000
GB    2340251       2/2000

(Continued)

OTHER PUBLICATIONS

Choi S. O. et al., "An integrated micro fluxgate magnetic sensor", Sensors and Actuators A, vol. 55(2):121-126 (Jul. 1996).

(Continued)

*Primary Examiner* — Daniel Miller
(74) *Attorney, Agent, or Firm* — Knobbe, Martens, Olson & Bear LLP

(57) ABSTRACT

A differential transformer type magnetic sensor includes a board, a drive coil, a first differential coil, and a second differential coil. The drive coil includes a planar coil in which a dimension of a first direction is smaller than that of a second direction, and is disposed on the board. The first differential coil includes a planar coil having the same shape as the drive coil, and is disposed on the board. The second differential coil includes a planar coil having the same shape as the drive coil, and is disposed on the board. The first differential coil and the second differential coil are electrically connected so that a direction of induced current flowing along the first differential coil and a direction of induced current flowing along the second differential coil are opposite to each other.

7 Claims, 14 Drawing Sheets

(56) References Cited

U.S. PATENT DOCUMENTS

| | | | |
|---|---|---|---|
| 6,043,644 A * | 3/2000 | de Coulon | G01P 3/488 324/164 |
| 6,148,156 A | 11/2000 | Matsumoto | |
| 6,429,651 B1 * | 8/2002 | Choi | G01R 33/04 324/225 |
| 6,463,223 B1 * | 10/2002 | Karakama | G03G 21/1867 324/658 |
| 2009/0058348 A1 | 3/2009 | Ryu | |

FOREIGN PATENT DOCUMENTS

| | | |
|---|---|---|
| JP | H08-123188 A | 5/1996 |
| JP | 10-104934 A | 4/1998 |
| JP | 2001-099654 | 4/2001 |
| JP | 2001-099654 A | 4/2001 |
| JP | 2001-165910 A | 6/2001 |
| JP | 2001-228118 A | 8/2001 |
| JP | 2002-296239 A | 10/2002 |
| JP | 2002-296890 A | 10/2002 |
| JP | 2006-106009 A | 4/2006 |
| JP | 2007-024553 A | 2/2007 |

OTHER PUBLICATIONS

Partial Search Report for European Application No. 13188240.9, mailed on Feb. 25, 2014.

S.O. Choi, et al., "An integrated micro fluxgate magnetic sensor," Sensors and Actuators A, Elsevier Sequoia S.A., Lausanne, CH, vol. 55, No. 2, Jul. 31, 1996.

The extended European Search Report issued by the European Patent Office on May 14, 2014 in the corresponding European patent application No. 13188240.9—16 pages.

Notice of Rejection mailed by Japan Patent Office on Mar. 3, 2015 in the corresponding Japanese patent application No. 2012-227992—9 pages.

The extended European search report issued by European Patent Office on Feb. 2, 2015 in the corresponding European patent application No. 14197174.7—10 pages.

* cited by examiner

DIFFERENTIAL TRANSFORMER TYPE MAGNETIC SENSOR AND IMAGE FORMING APPARATUS

INCORPORATION BY REFERENCE

This application claims priority to Japanese Patent Application No. 2012-227992 filed on Oct. 15, 2012, the entire contents of which are incorporated by reference herein.

BACKGROUND

The present disclosure relates to a differential transformer type magnetic sensor using a planar coil and an image forming apparatus that detects a residual quantity of toner contained in a development part using the magnetic sensor.

In image forming apparatuses using toner as a developer, a magnetic sensor is used for detection of a residual quantity or a density of the toner. There are various types of magnetic sensors. A differential transformer type magnetic sensor has a configuration in which a drive coil, a differential coil functioning as a detection coil, and another differential coil functioning as a reference coil are disposed on the same core.

As the coils are formed into planar coils, the differential transformer type magnetic sensor can be made compact. As the differential transformer type magnetic sensor using the planar coils, a magnetic sensor in which a first coil (drive coil), a second coil (differential coil), a third coil (differential coil), and a fourth coil (drive coil) are disposed on a first layer, a second layer, a third layer, and a fourth layer respectively, and in which an insulating board is disposed between the neighboring layers is proposed.

Further, as the differential transformer type magnetic sensor using the planar coils, a magnetic sensor in which a first coil (drive coil) and a third coil (differential coil) are disposed in parallel on one surface of an insulating magnetic board, and in which a second coil (drive coil) and a fourth coil (differential coil) are disposed in parallel on the other surface of an insulating magnetic board is also proposed.

SUMMARY

Technology that further improves the aforementioned technology is proposed as one aspect of the present disclosure.

A differential transformer type magnetic sensor according to one aspect of the present disclosure includes a board, a drive coil, a first differential coil, and second differential coil.

The drive coil includes a polygonal planar coil in which a dimension of a first direction which is one of longitudinal and transverse dimensions is smaller than that of a second direction which is the other of the longitudinal and transverse dimensions, and is disposed on the board.

The first differential coil includes a planar coil along which induced current flows due to magnetic flux generated as drive current flows along the drive coil and which has the same shape as the drive coil, and is disposed on the board.

The second differential coil includes a planar coil along which induced current flows due to magnetic flux generated as drive current flows along the drive coil and which has the same shape as the drive coil, and is disposed on the board.

The first differential coil and the second differential coil are electrically connected so that a direction of the induced current flowing along the first differential coil and a direction of the induced current flowing along the second differential coil are opposite to each other.

The differential transformer type magnetic sensor is configured so that, when viewed from a thickness direction of the board, an array region of the drive coil, an array region of the first differential coil, and an array region of the second differential coil overlap.

Further, an image forming apparatus according to another aspect of the present disclosure includes a differential transformer type magnetic sensor having a board, a drive coil, a first differential coil, and a second differential coil.

The drive coil includes a planar coil in which a dimension of a first direction which is one of longitudinal and transverse dimensions is smaller than that of a second direction which is the other of the longitudinal and transverse dimensions, and is disposed on the board.

The first differential coil includes a planar coil along which induced current flows due to magnetic flux generated as drive current flows along the drive coil and which has the same shape as the drive coil, and is disposed on the board.

The second differential coil includes a planar coil along which induced current flows due to magnetic flux generated as drive current flows along the drive coil and which has the same shape as the drive coil, and is disposed on the board.

The first differential coil and the second differential coil are electrically connected so that a direction of the induced current flowing along the first differential coil and a direction of the induced current flowing along the second differential coil are opposite to each other.

The differential transformer type magnetic sensor is disposed on a development part with the first direction set to be vertical and with the second direction set to be horizontal, and provides an output corresponding to a height of toner contained in the development part.

DETAILED DESCRIPTION

Hereinafter, an image forming apparatus and a differential transformer type magnetic sensor according to an embodiment in an aspect of the present disclosure will be described with reference to the drawings.

Figure 1:
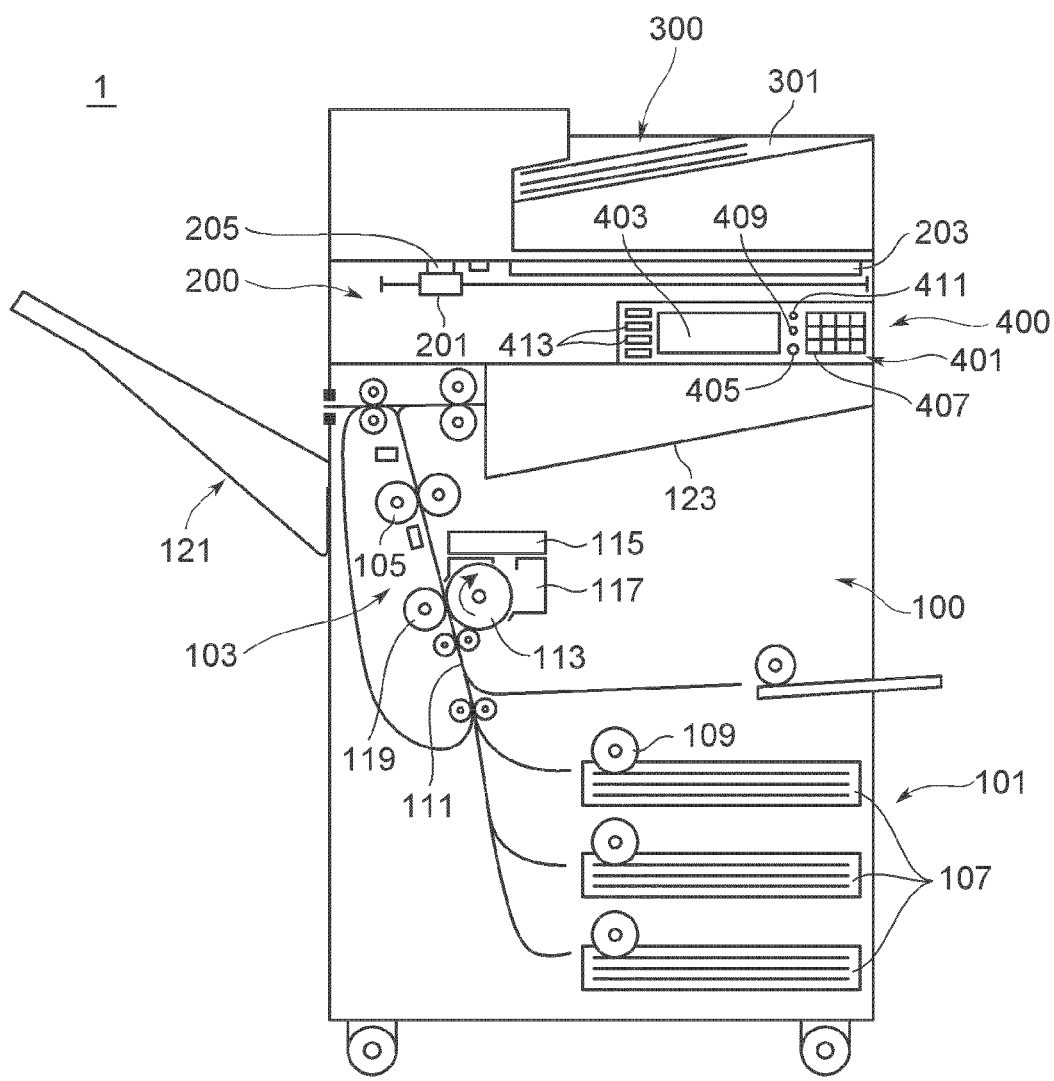
FIG. 1 is a diagram showing a schematic internal structure of an image forming apparatus according to an embodiment of the present disclosure.

FIG. 1 is a diagram showing a schematic internal structure of an image forming apparatus 1 according to an embodiment of the present disclosure. The image forming apparatus 1 may be applied to a digital multifunction device having, for instance, a copy function, a printer function, a scanner function, and a facsimile function. The image forming apparatus 1 includes an apparatus main body 100, a document scanning unit 200 disposed on the apparatus main body 100, a document feeding unit 300 disposed on the document scanning unit 200, and an operating unit 400 disposed in an upper front face of the apparatus main body 100.

The document feeding unit 300 functions as an auto document feeder, and can send a plurality of documents placed on a document loading part 301 so as to be continuously scanned by the document scanning unit 200.

The document scanning unit 200 includes a carriage 201 on which an exposure lamp is mounted, a platen 203 made up of a transparent member such as glass, a charge coupled device (CCD) sensor (not shown), and a document scanning slit 205. When the document loaded on the platen 203 is scanned, the document is scanned by the CCD sensor while the carriage 201 is moved in a longitudinal direction of the platen 203. In contrast, when the document fed from the document feeding unit 300 is scanned, the carriage 201 is moved to a position opposite to the document scanning slit 205, and the document sent from the document feeding unit 300 is scanned through the document scanning slit 205 by the CCD sensor. The CCD sensor outputs the scanned document as image data.

The apparatus main body 100 includes a paper storage unit 101, an image forming unit 103, and a fixing unit 105. The paper storage unit 101 is disposed at a lowest portion of the apparatus main body 100 and includes paper trays 107, each of which can store a stack of paper. In the stack of paper stored in each paper tray 107, the topmost paper is sent toward the paper conveyance path 111 by driving of a pickup roller 109. The paper is conveyed to the image forming unit 103 through the paper conveyance path 111.

The image forming unit 103 forms a toner image on the conveyed paper. The image forming unit 103 includes a photosensitive drum 113, an exposure part 115, a development part 117, and a transfer part 119. The exposure part 115 generates light modulated in response to image data (image data output from the document scanning unit 200, image data transmitted from a personal computer, facsimiled image data, etc.), and scans a circumferential surface of the photosensitive drum (image carrier) 113 charged uniformly. Thereby, an electrostatic latent image corresponding to the image data is formed on the circumferential surface of the photosensitive drum 113. In this state, the toner is supplied from the development part 117 to the circumferential surface of the photosensitive drum 113. Thereby, a toner image corresponding to the image data is formed on the circumferential surface of the photosensitive drum 113. This toner image is transferred to the paper, which is conveyed from the paper storage unit 101 described above, by the transfer part 119.

The paper to which the toner image is transferred is sent to the fixing unit 105. In the fixing unit 105, heat and pressure are applied to the toner image and the paper, and the toner image is fixed to the paper. The paper is ejected to a stack tray 121 or an eject tray 123. In this way, the image forming apparatus 1 prints a monochromic image.

The operating unit 400 includes an operation key part 401 and a display part 403. The display part 403 has a touch panel function, and a screen including a soft key is displayed. A user operates the soft key while watching the screen, thereby performing a setting required to carry out a function such as copying.

The operation key part 401 is provided with operation keys made up of hard keys. In detail, a start key 405, a numeric keypad 407, a stop key 409, a reset key 411, and a function switching key 413 for switching the copy, the printer, the scanner, and the facsimile are provided.

The start key 405 is a key that initiates an operation such as copying or facsimile transmission. The numeric keypad 407 is a keypad that inputs numbers such as the number of copies or a facsimile number. The stop key 409 is a key that stops, for instance, a copy operation midway. The reset key 411 is a key that returns set contents to a default state.

The function switching key 413 includes a copy key and a sending key, and is a key that mutually switches a copy function and a sending function. When the copy key is operated, an initial screen for copy is displayed on the display part 403. When the sending key is operated, an initial screen for facsimile transmission and mail transmission is displayed on the display part 403.

Figure 2:
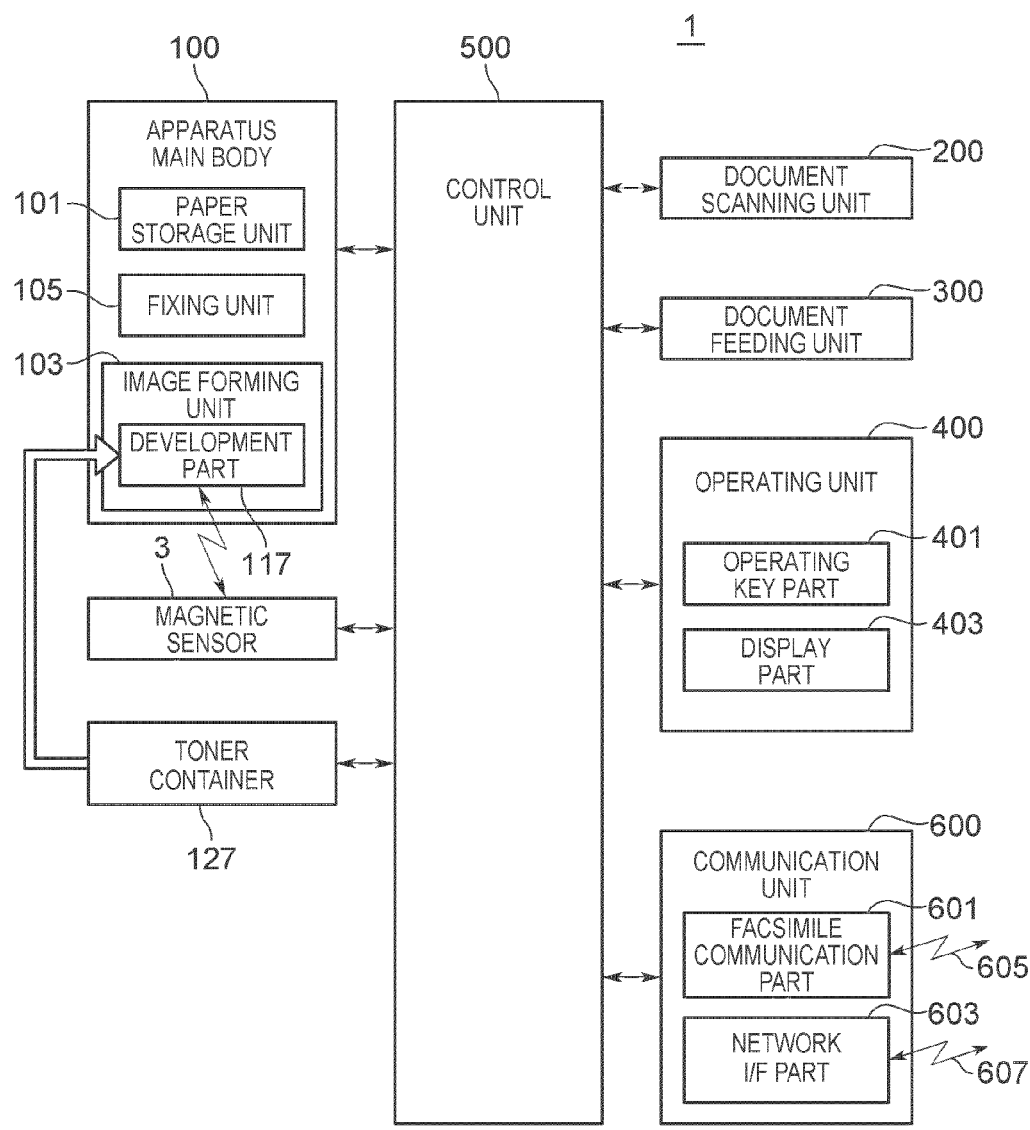
FIG. 2 is a block diagram showing a configuration of the image forming apparatus shown in FIG. 1.

FIG. 2 is a block diagram showing a configuration of the image forming apparatus 1 shown in FIG. 1. The image forming apparatus 1 has a configuration in which the apparatus main body 100, the differential transformer type magnetic sensor 3, the toner container 127, the document scanning unit 200, the document feeding unit 300, the operating unit 400, a control unit 500, and a communication unit 600 are mutually connected by buses. Since the apparatus main body 100, the document scanning unit 200, the document feeding unit 300, and the operating unit 400 have already been described, a description thereof will be omitted.

Toner (magnetic one-component developer) is contained in the toner container 127, and is supplied from the toner container 127 to the development part 117.

The differential transformer type magnetic sensor 3 is the differential transformer type magnetic sensor according to one embodiment of the present disclosure, detects a change in height of the toner in the development part 117, and measures a toner residual quantity in the development part 117 based on the detection. The differential transformer type magnetic sensor 3 will be described in detail below.

The control unit 500 includes a central processing unit (CPU), a read only memory (ROM), a random access memory (RAM), and an image memory. The CPU carries out control required to operate the image forming apparatus 1 on the aforementioned components of the image forming apparatus 1 including the apparatus main body 100. The ROM stores software required to control the operation of the image forming apparatus 1. The RAM is used to temporarily store data generated during execution of the software and to store application software. The image memory temporarily stores image data (image data output from the document scanning unit 200, image data sent from the personal computer, facsimiled image data, etc.).

The communication unit 600 includes a facsimile communication part 601 and a network interface (I/F) part 603. The facsimile communication part 601 includes a network control unit (NCU) that controls connection of a phone line with a counterpart facsimile and a modulation and demodulation circuit that modulates and demodulates a signal for facsimile communication. The facsimile communication part 601 is connected to a phone line 605.

The network I/F part 603 is connected to a local area network (LAN) 607. The network I/F part 603 is a communication interface circuit for conducting communication between the LAN 607 and a terminal device such as a personal computer connected to the LAN 607.

Figure 3:
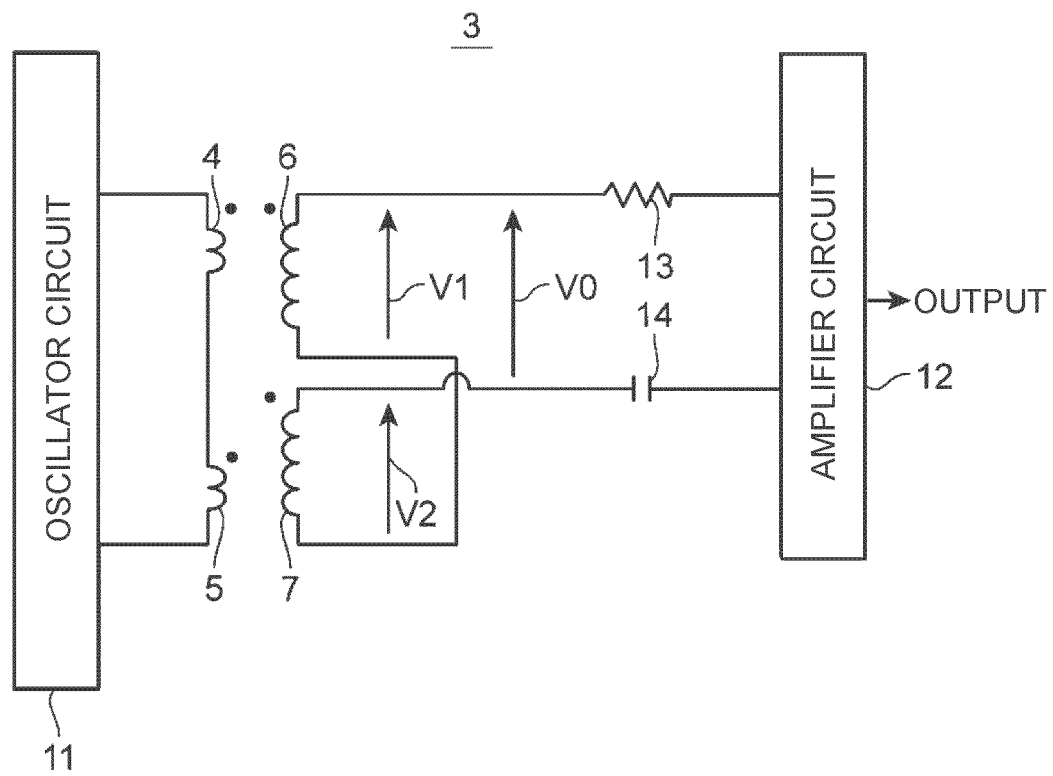
FIG. 3 is a circuit diagram of a differential transformer type magnetic sensor according to the present embodiment.

FIG. 3 is a circuit diagram of the differential transformer type magnetic sensor 3 (which may hereinafter be referred to as "magnetic sensor 3") according to the present embodiment. The differential transformer type magnetic sensor 3 includes a first drive coil 4, a second drive coil 5, a first differential coil 6 functioning as a reference coil, a second differential coil 7 functioning as a detection coil, an oscillator circuit 11, an amplifier circuit 12, a resistor 13, and a capacitor 14.

The oscillator circuit 11 generates a high-frequency drive current that drives the first drive coil 4 and the second drive coil 5. The first drive coil 4 and the second drive coil 5 are connected in series. One end of the first drive coil 4 and one end of the second drive coil 5 are connected so that, when the drive current flows to the first drive coil 4 and the second drive coil 5, magnetic flux generated by the first drive coil 4 and magnetic flux generated by the second drive coil 5 have the same direction (in other words, a direction of an induced current flowing along the first drive coil 4 and a direction of a drive current flowing along the second drive coil 5 are identical to each other). Thereby, the magnetic flux generated by the first drive coil 4 and the magnetic flux generated by the second drive coil 5 are prevented from being offset. The other end of the first drive coil 4 and the other end of the second drive coil 5 are connected to the oscillator circuit 11.

The first differential coil (reference coil) 6 is magnetically coupled with the first drive coil 4. The second differential coil (detection coil) 7 is magnetically coupled with the second drive coil 5. The first differential coil 6 and the second differential coil 7 are differentially connected in series. In other words, the first differential coil 6 and the second differential coil 7 are electrically connected so that directions of induced currents flowing along the first differential coil 6 and the second differential coil 7 are opposite to each other. Thereby, a differential voltage V0 (=an electromotive voltage V1 of the first differential coil 6 minus an electromotive voltage V2 of the second differential coil 7) is input to the amplifier circuit 12.

The other end of the first differential coil 6 is connected to the amplifier circuit 12 via the resistor 13, and the other end of the second differential coil 7 is connected to the amplifier circuit 12 via the capacitor 14. The resistor 13 is connected to a base of a bipolar transistor within the amplifier circuit 12, and is used to set a gain of the amplifier circuit 12.

The capacitor 14 functions to cut off a direct current component of the differential voltage V0. Thereby, only an alternate current component of the differential voltage V0 is input to the amplifier circuit 12.

An operation of the magnetic sensor 3 will be briefly described. When a drive current generated by the oscillator circuit 11 flows to the first drive coil 4 and the second drive coil 5, the electromotive voltage V1 is generated at the first differential coil 6, and the electromotive voltage V2 is generated at the second differential coil 7. When toner is present in the vicinity of the second differential coil 7, the electromotive voltage V2 is higher than the electromotive voltage V1. As such, the differential voltage V0 does not become 0 V. The differential voltage V0 is amplified by the amplifier circuit 12, and using a signal that is output from the amplifier circuit 12, a residual quantity of the toner is detected.

Figure 4:
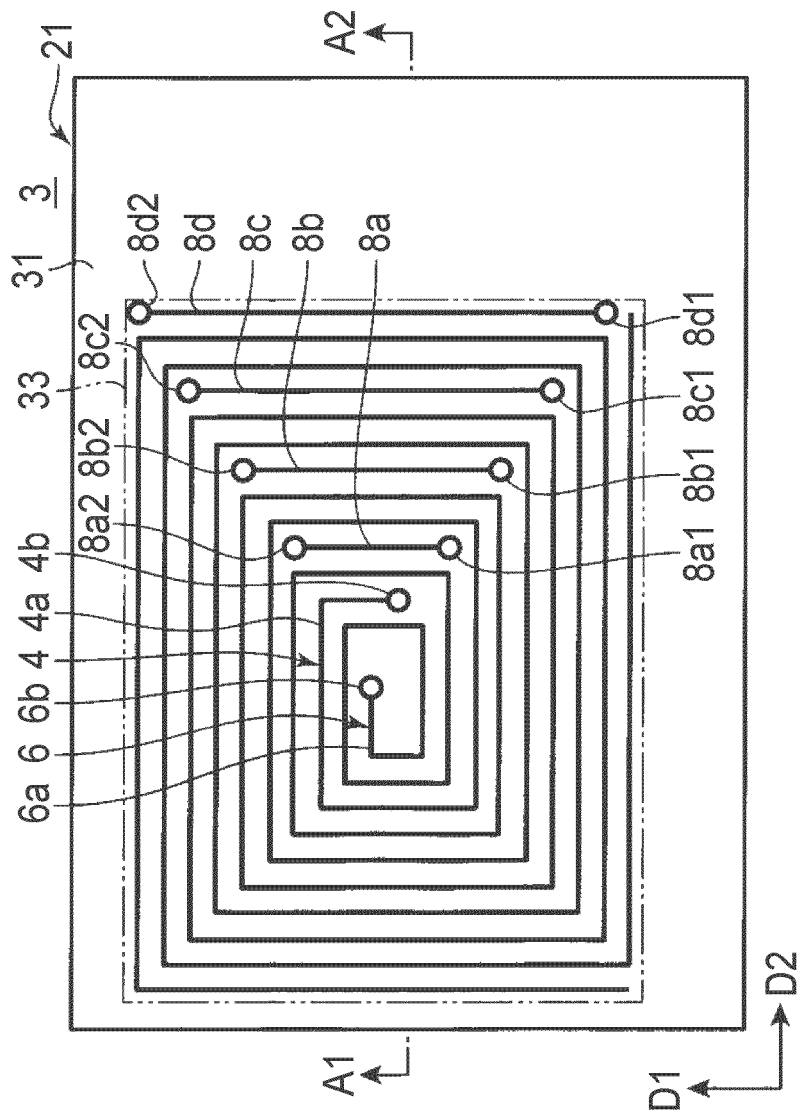
FIG. 4 is a plan view showing a layout of a first drive coil, a first differential coil, and connection patterns provided for the differential transformer type magnetic sensor according to the present embodiment.
Figure 5:
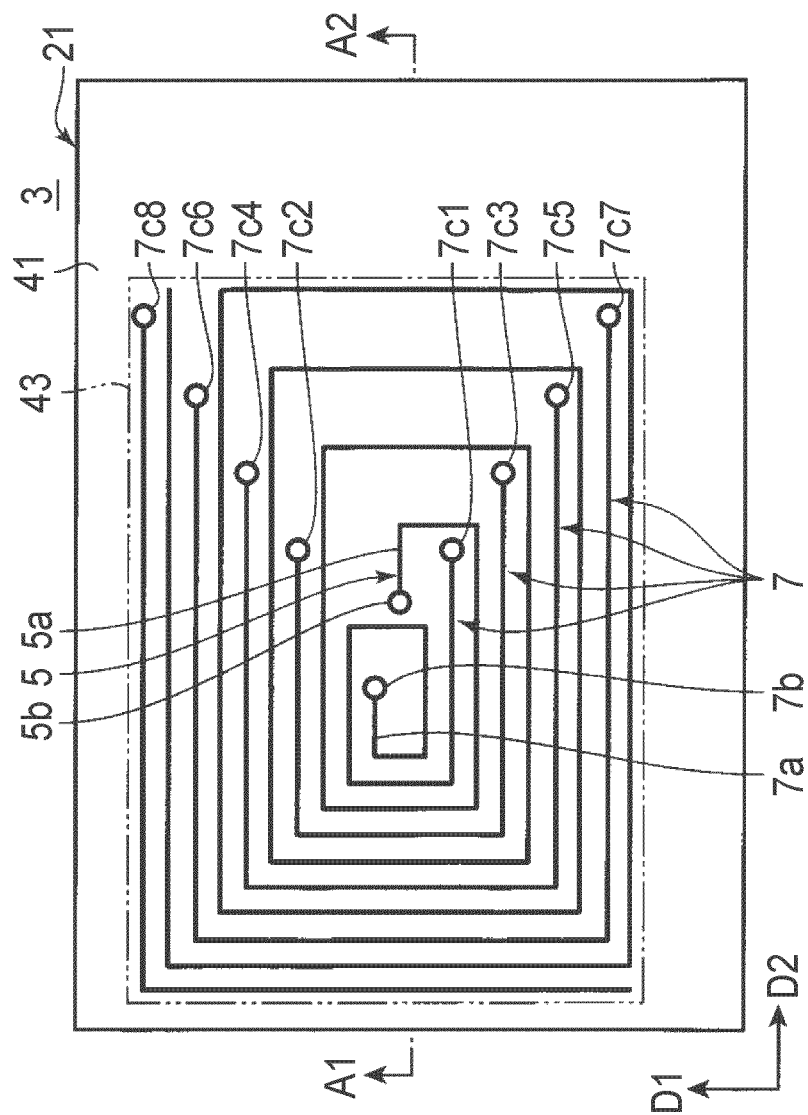
FIG. 5 is a plan view showing a layout of a second drive coil and a second differential coil provided for the differential transformer type magnetic sensor according to the present embodiment.

Next, a structure of the differential transformer type magnetic sensor 3 will be described. FIG. 4 is a plan view showing a layout of the first drive coil 4, the first differential coil 6, and connection patterns 8a, 8b, 8c, and 8d provided for the magnetic sensor 3. FIG. 5 is a plan view showing a layout of the second drive coil 5 and the second differential coil 7 provided for the magnetic sensor 3.

The magnetic sensor 3 includes a board 21, the first drive coil 4, the first differential coil 6, connection patterns 8a, 8b, 8c, and 8d, the second drive coil 5, and the second differential coil 7. When there is no need to distinguish them, the connection patterns 8a, 8b, 8c, and 8d are referred to as connection patterns 8.

In the board 21 having a rectangular shape, a direction of a short side thereof is defined as a first direction D1, and a direction of a long side thereof is defined as a second direction D2. The first direction D1 and the second direction D2 are perpendicular to each other. The board 21 includes a first surface 31 and a second surface 41 located on the opposite side of the first surface 31. FIG. 5 is a diagram looking through the second surface 41, the second drive coil 5, and the second differential coil 7 from a side of the first surface 31.

The first drive coil 4, the first differential coil 6, and the connection patterns 8 are disposed on an array region 33 of the first surface 31. The second drive coil 5 and the second differential coil 7 are disposed on an array region 43 of the second surface 41. When viewed from a thickness direction of the board 21, the array region of the first drive coil 4, the array region of the first differential coil 6, the array region of the second drive coil 5, and the array region of the second differential coil 7 overlap.

Figure 6:
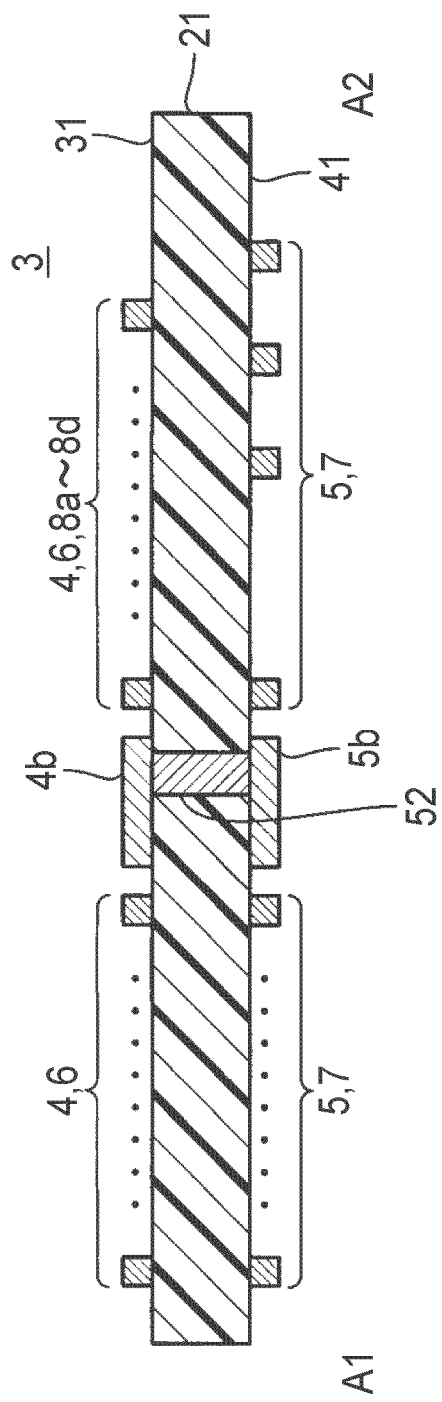
FIG. 6 is a cross-sectional view obtained by cutting a board along line A1-A2.

A view obtained by cutting the board 21 along line A1-A2 is FIG. 6. The board 21 is an insulating single-layer printed circuit board.

Figure 7A:
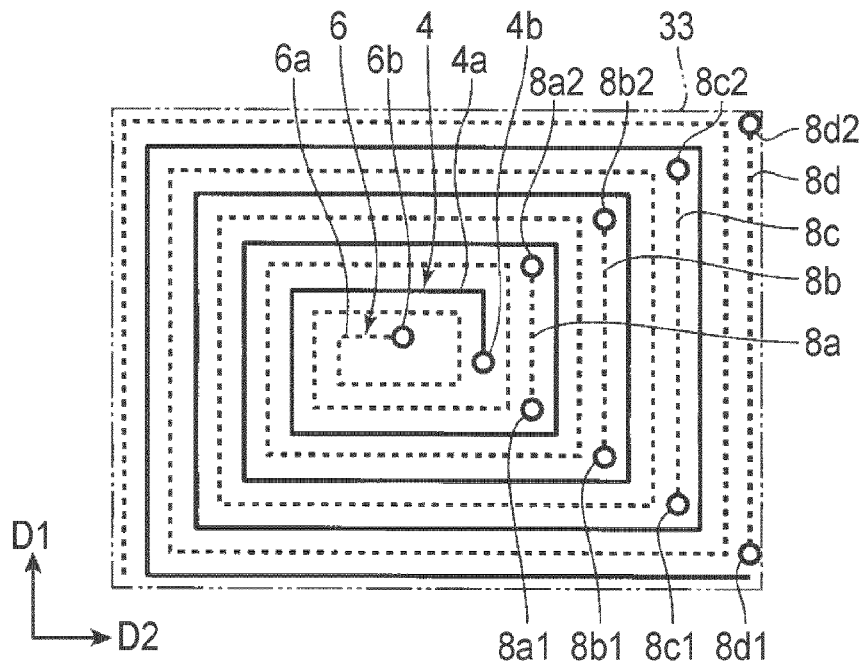
FIG. 7A and FIG. 7B are a plan view showing the first drive coil separately from other coils.
Figure 7B:
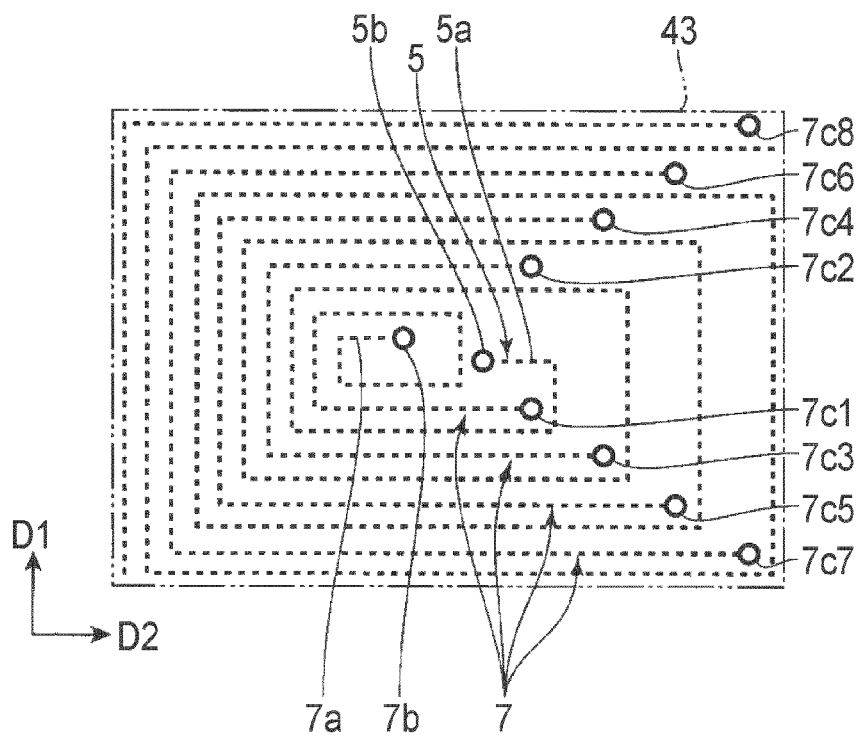

The first drive coil 4 will be described. FIG. 7A and FIG. 7B are a plan view showing the first drive coil 4 separately from other coils. FIG. 7A shows the array region 33 of the first surface 31, and FIG. 7B shows the array region 43 of the second surface 41. A line indicated by a solid line shows the first drive coil 4, and a line indicated by a dotted line shows the first differential coil 6, the connection patterns 8, the second drive coil 5, and the second differential coil 7.

The first drive coil 4 is made up of a wire rod 4a wound in a rectangular shape, and the wire rod 4a is patterned so that a rectangular dimension is gradually increased in a counterclockwise direction using a terminal 4b as a starting point.

Figure 8A:
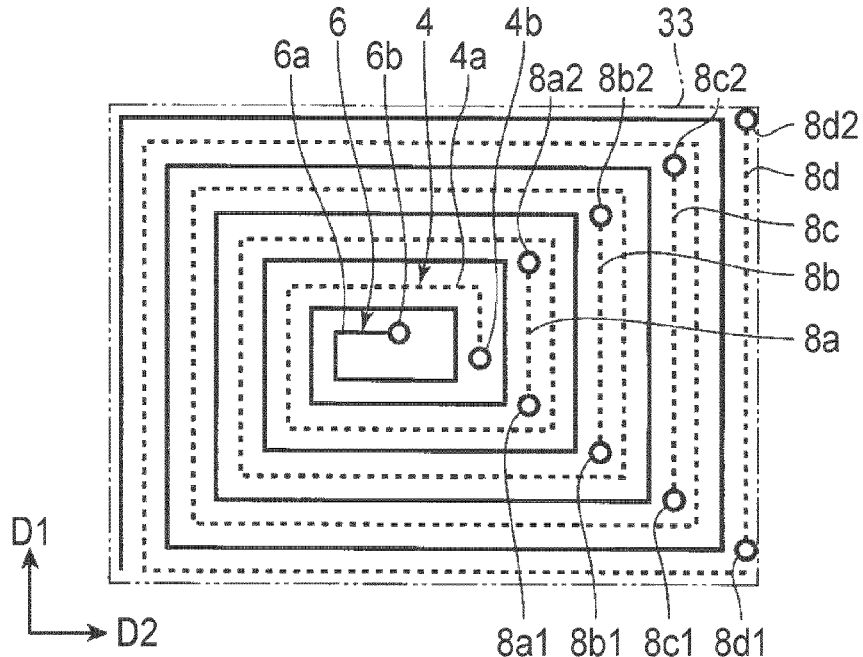
FIG. 8A and FIG. 8B are a plan view showing the first differential coil separately from other coils.
Figure 8B:
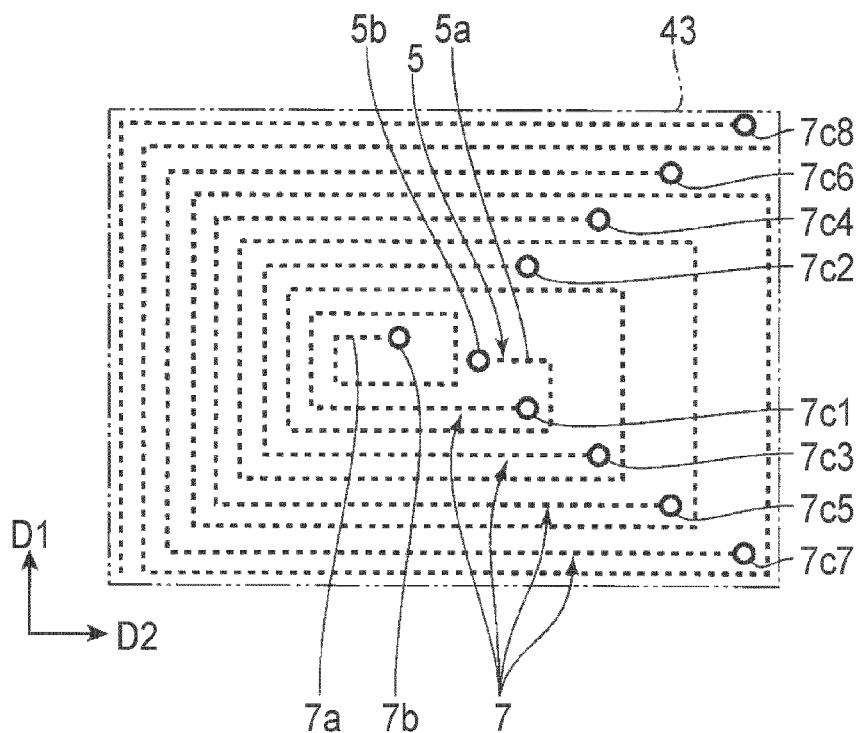

The first differential coil 6 will be described. FIG. 8A and FIG. 8B are a plan view showing the first differential coil 6 separately from other coils. FIG. 8A shows the array region 33 of the first surface 31, and FIG. 8B shows the array region 43 of the second surface 41. A line indicated as a solid line shows the first differential coil 6, and lines indicated as dotted lines show the first drive coil 4, the connection patterns 8, the second drive coil 5, and the second differential coil 7.

The first differential coil 6 is made up of a wire rod 6*a* wound in a rectangular shape, and the wire rod 6*a* is patterned so that a rectangular dimension is gradually increased in a counterclockwise direction using a terminal 6*b* as a starting point.

The wire rod 4*a* constituting the first drive coil 4 and the wire rod 6*a* constituting the first differential coil 6 are wound in parallel in the same direction. Thereby, the wire rod 4*a* constituting the first drive coil 4 and the wire rod 6*a* constituting the first differential coil 6 are alternately disposed.

Figure 9A:
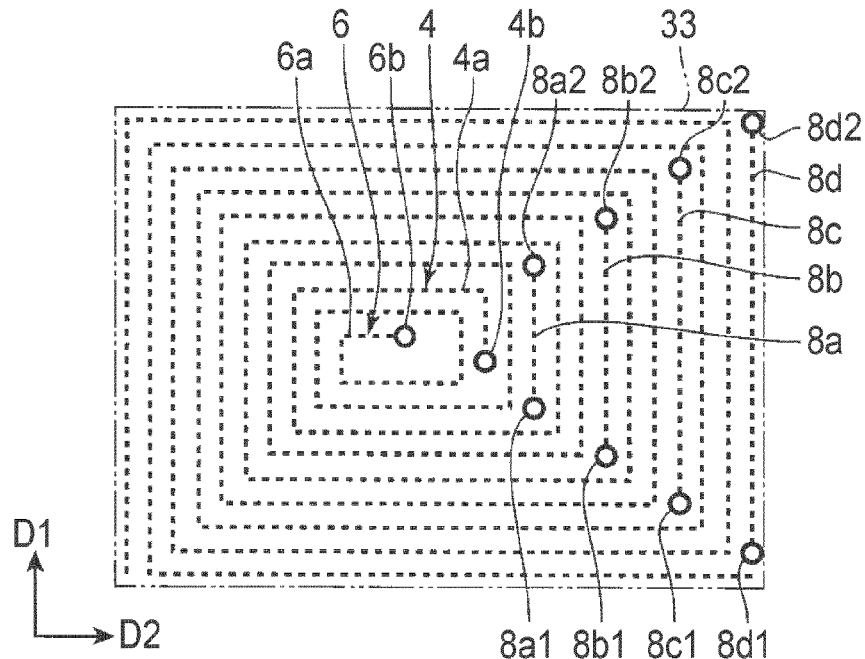
FIG. 9A and FIG. 9B are a plan view showing the second drive coil separately from other coils.
Figure 9B:
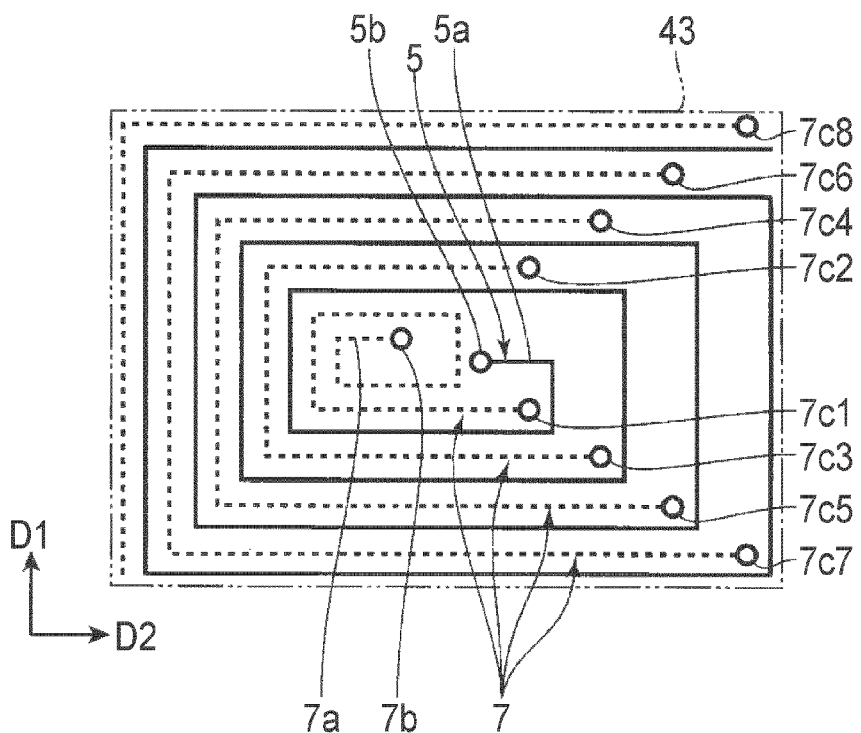

The second drive coil 5 will be described. FIG. 9A and FIG. 9B are a plan view showing the second drive coil 5 separately from other coils. FIG. 9A shows the array region 33 of the first surface 31, and FIG. 9B shows the array region 43 of the second surface 41. A line indicated as a solid line shows the second drive coil 5, and lines indicated as dotted lines show the first drive coil 4, the first differential coil 6, the connection patterns 8, and the second differential coil 7.

When viewed from the side of the first surface 31, the second drive coil 5 is wound in the opposite direction of the first drive coil 4. To be specific, the second drive coil 5 is made up of a wire rod 5*a* wound in a rectangular shape, and the wire rod 5*a* is patterned so that a rectangular dimension is gradually increased in a clockwise direction using a terminal 5*b* as a starting point.

As shown in FIG. 6, the terminal 5*b* of the second drive coil 5 is electrically connected to the terminal 4*b* of the first drive coil 4 by a first connecting member 52 formed in the board 21 in a penetrated state. Thereby, the second drive coil 5 is electrically connected to the first drive coil 4 so that a drive current flows in the same direction as a drive current flowing along the first drive coil 4.

Figure 10A:
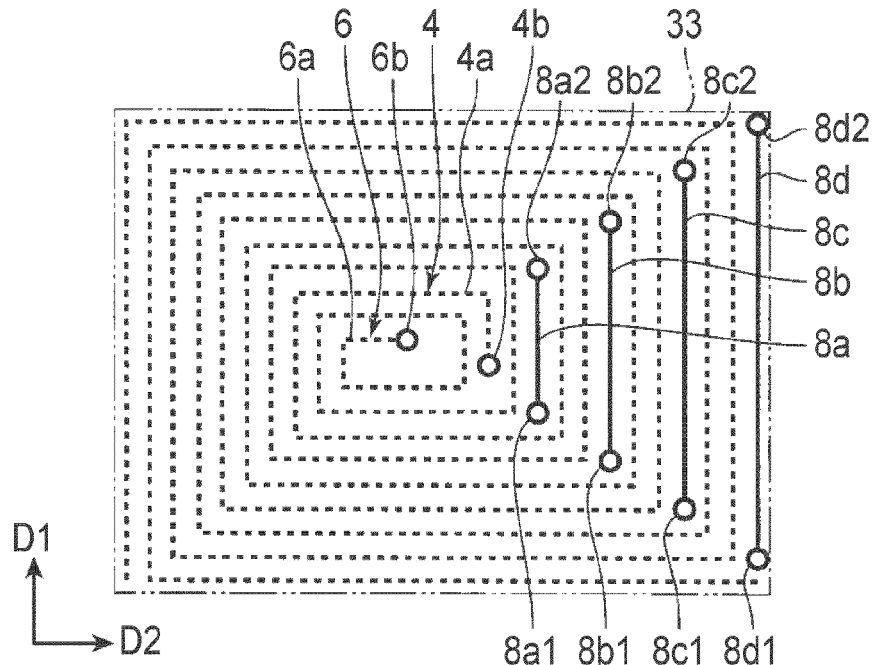
FIG. 10A and FIG. 10B are a plan view showing the second differential coil separately from other coils.
Figure 10B:
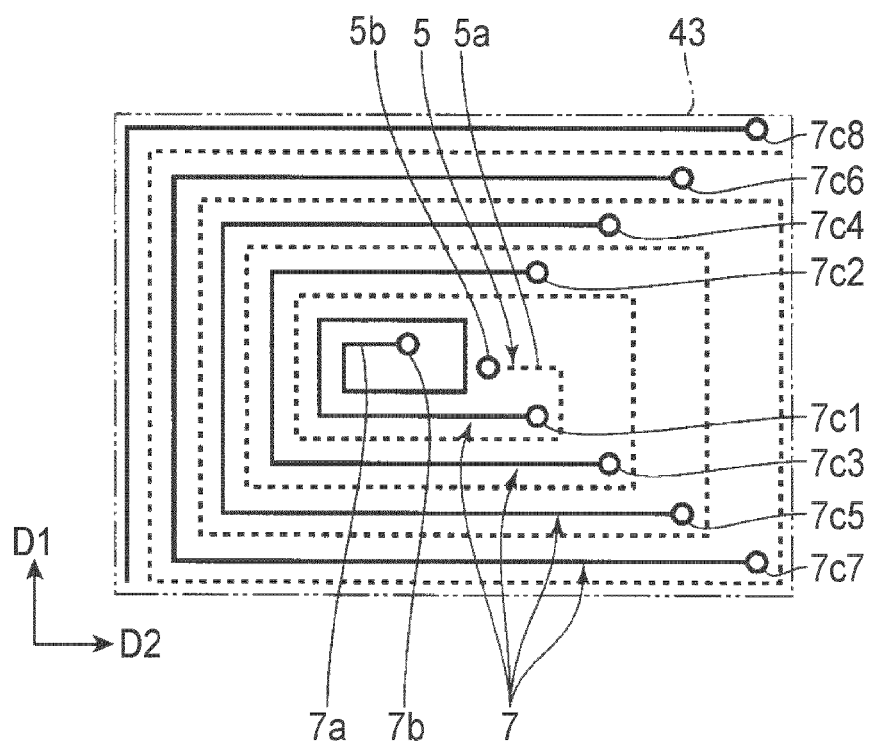

The second differential coil 7 will be described. FIG. 10A and FIG. 10B are a plan view showing the second differential coil 7 separately from other coils. FIG. 10A shows the array region 33 of the first surface 31, and FIG. 10B shows the array region 43 of the second surface 41. A line indicated as a solid line shows the second differential coil 7, and lines indicated as dotted lines show the first drive coil 4, the first differential coil 6, and the second drive coil 5.

The second differential coil 7 is wound in the opposite direction of the second drive coil 5. To be specific, the second differential coil 7 is made up of a wire rod 7*a* wound in a rectangular shape, and the wire rod 7*a* is patterned so that a rectangular dimension is gradually increased in a counterclockwise direction using a terminal 7*b* as a starting point. The wire rod 7*a* constituting the second differential coil 7 and the wire rod 5*a* constituting the second drive coil 5 are alternately disposed.

The second differential coil 7 is an intermittent pattern disposed on the second surface 41. This is for the following reason. Since the second differential coil 7 is wound in the opposite direction of the second drive coil 5, the second differential coil 7 and the second drive coil 5 intersect. To prevent the second differential coil 7 and the second drive coil 5 from coming into contact with each other, the second differential coil 7 and the second drive coil 5 are grade-separated using the connection patterns 8.

As shown in FIG. 10B, in the array region 43 of the second surface 41, the second differential coil 7 is disconnected at a place at which the second differential coil 7 is grade-separated from the second drive coil 5, and terminals 7*c*1 to 7*c*8 are formed at the disconnected portions. The terminal 7*c*1 and the terminal 7*c*2, the terminal 7*c*3 and the terminal 7*c*4, the terminal 7*c*5 and the terminal 7*c*6, and the terminal 7*c*7 and the terminal 7*c*8 are provided at positions parallel to the first direction D1.

As shown in FIG. 10A, the connection patterns 8 are linear patterns extending in the first direction D1. The connection patterns 8 are disposed at places that are opposite to the place at which the aforementioned second differential coil 7 is grade-separated from the second drive coil 5.

Terminals 8*a*1 and 8*a*2 of opposite ends of the connection pattern 8*a* are electrically connected to the terminals 7*c*1 and 7*c*2 shown in FIG. 10B, respectively. Terminals 8*b*1 and 8*b*2 of opposite ends of the connection pattern 8*b* are electrically connected to the terminals 7*c*3 and 7*c*4 shown in FIG. 10B, respectively. Terminals 8*c*1 and 8*c*2 of opposite ends of the connection pattern 8*c* are electrically connected to the terminals 7*c*5 and 7*c*6 shown in FIG. 10B, respectively. Terminals 8*d*1 and 8*d*2 of opposite ends of the connection pattern 8*d* are electrically connected to the terminals 7*c*7 and 7*c*8 shown in FIG. 10B, respectively. These connections are performed by third connecting members (not shown). The third connecting members are connecting plugs formed in the board 21 in a penetrated state, like the first connecting member 52 shown in FIG. 6.

The terminal 6*b* of the first differential coil 6 and the terminal 7*b* of the second differential coil 7 are electrically connected by a second connecting member (not shown). The second connecting member is a connecting plug formed in the board 21 in a penetrated state, like the first connecting member 52 shown in FIG. 6.

To increase precision of the magnetic sensor 3, it is necessary to greatly change the differential voltage V0 within an output range (e.g., from 0.2 to 3.3 V) of the differential voltage V0 shown in FIG. 3. To this end, in a state in which no magnet is present in the vicinity of the magnetic sensor 3, the electromotive voltage V1 generated by the first differential coil 6 and the electromotive voltage V2 generated by the second differential coil 7 are preferably proportional to each other. To cause the electromotive voltage V1 and the electromotive voltage V2 to be proportional to each other, the electromotive voltage V1 and the electromotive voltage V2 are set as follows.

The number of turns of the first differential coil 6 and the number of turns of the second differential coil 7 are made identical to each other. To cause the pattern of the first differential coil 6 and the pattern of the second differential coil 7 to overlap via the board 21 as much as possible, the first differential coil 6 is disposed on the first surface 31, and the second differential coil 7 is disposed on the second surface 41. Likewise, the number of turns of the first drive coil 4 and the number of turns of the second drive coil 5 are made identical to each other. To cause the pattern of the first drive coil 4 and the pattern of the second drive coil 5 to overlap via the board 21 as much as possible, the first drive coil 4 is disposed on the first surface 31, and the second drive coil 5 is disposed on the second surface 41.

The first drive coil 4, the first differential coil 6, the second drive coil 5, and the second differential coil 7 are rectangular planar coils, in each of which a direction of a short side thereof is the first direction D1, and a direction of a long side thereof is the second direction D2.

The planar coils used as the first drive coil 4, the first differential coil 6, the second drive coil 5, and the second differential coil 7 have been described as rectangular planar coils as an example, but not limited thereto. The planar coils used as the first drive coil 4, the first differential coil 6, the second drive coil 5, and the second differential coil 7 are planar coils in which a dimension of the first direction D1 which is one of longitudinal and transverse dimensions is smaller than that of the second direction D2 which is the other of the longitudinal and transverse dimensions.

Figure 11:
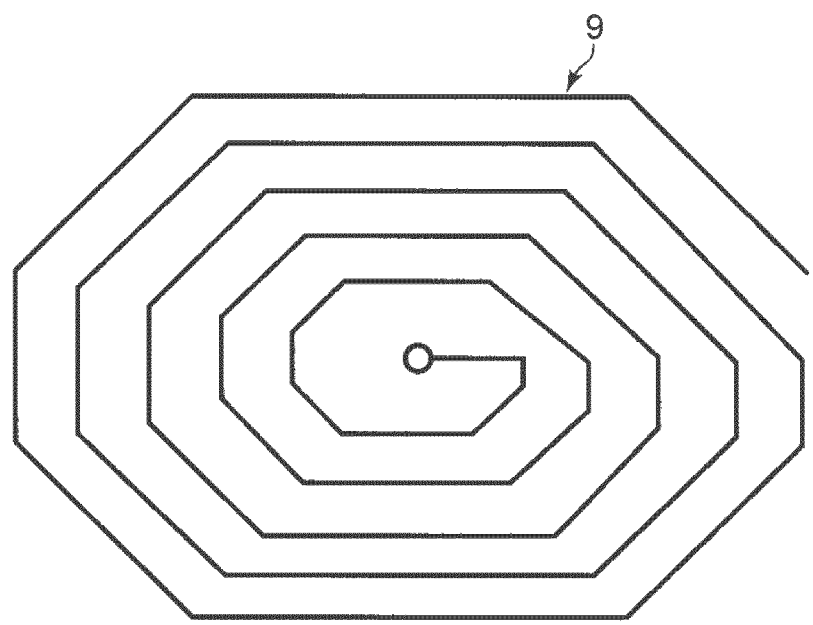
FIG. 11 is a plan view of a flat octagonal planar coil.

This planar coil includes a planar coil 9 having a flat octagonal shape shown in FIG. 11. Further, although not shown, this planar coil may be a planar coil having a flat polygonal shape with more than four angles (e.g., a flat hexagonal shape), or a planar coil having an elliptical shape.

Figure 12:
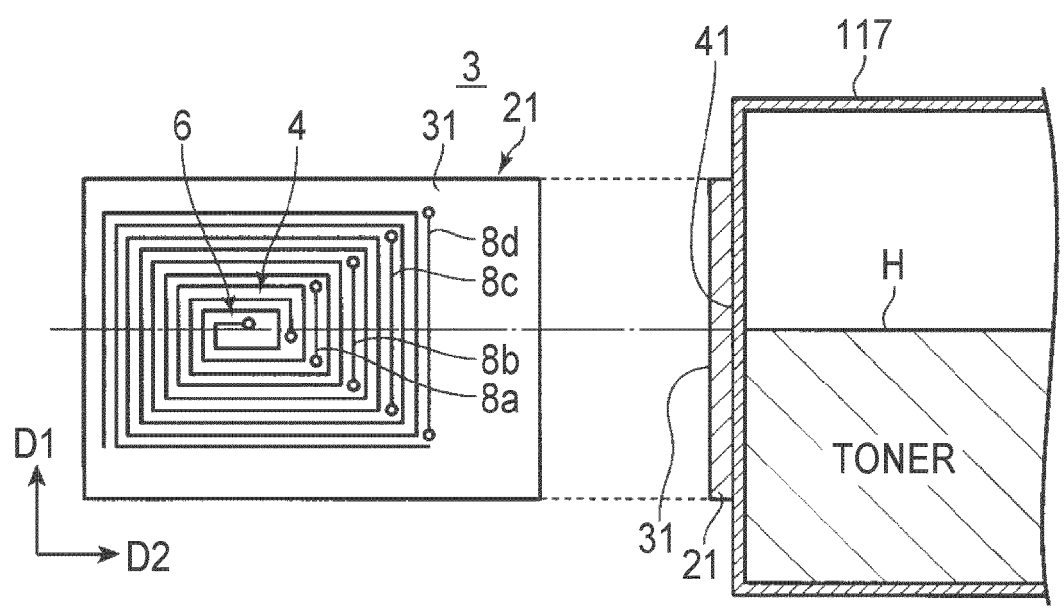
FIG. 12 is a plan view of the differential transformer type magnetic sensor according to the present embodiment, and a cross-sectional view showing a cross section of the magnetic sensor mounted on a development part.

FIG. 12 is a plan view of the differential transformer type magnetic sensor 3 and a cross-sectional view showing a cross section of the magnetic sensor 3 mounted on the development part 117. The magnetic sensor 3 is mounted on an outer lateral face of a cabinet of the development part 117 with the first direction D1 that is the direction of the short side of each of the first drive coil 4, the first differential coil 6, the second drive coil 5, and the second differential coil 7 set to be vertical and with the second direction D2 that is the direction of the long side of each of these coils set to be horizontal.

A line indicated by a symbol H denotes a reference height of the toner (one-component developer) contained in the development part 117. The magnetic sensor 3 is disposed on the outer lateral face of the cabinet of the development part 117 so that a central portion of each of the first drive coil 4, the first differential coil 6, the second drive coil 5, and the second differential coil 7 is located at a position of the reference height H.

Figure 13:
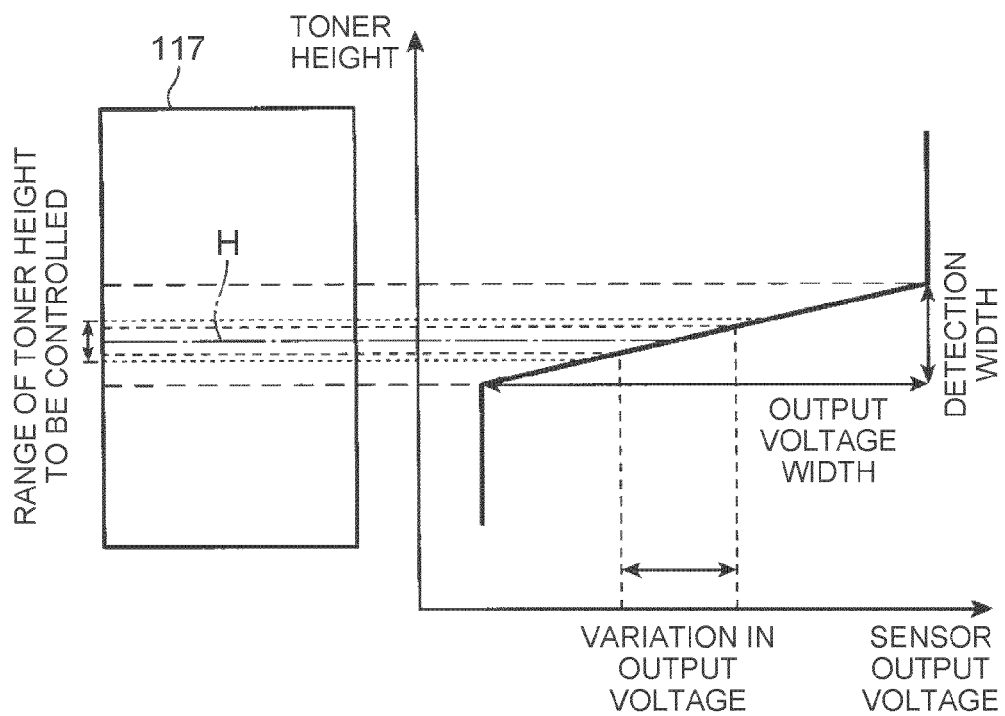
FIG. 13 is a graph showing a relation between an output voltage of the differential transformer type magnetic sensor provided for the image forming apparatus according to the present embodiment and a height of toner contained in the development part.
Figure 14:
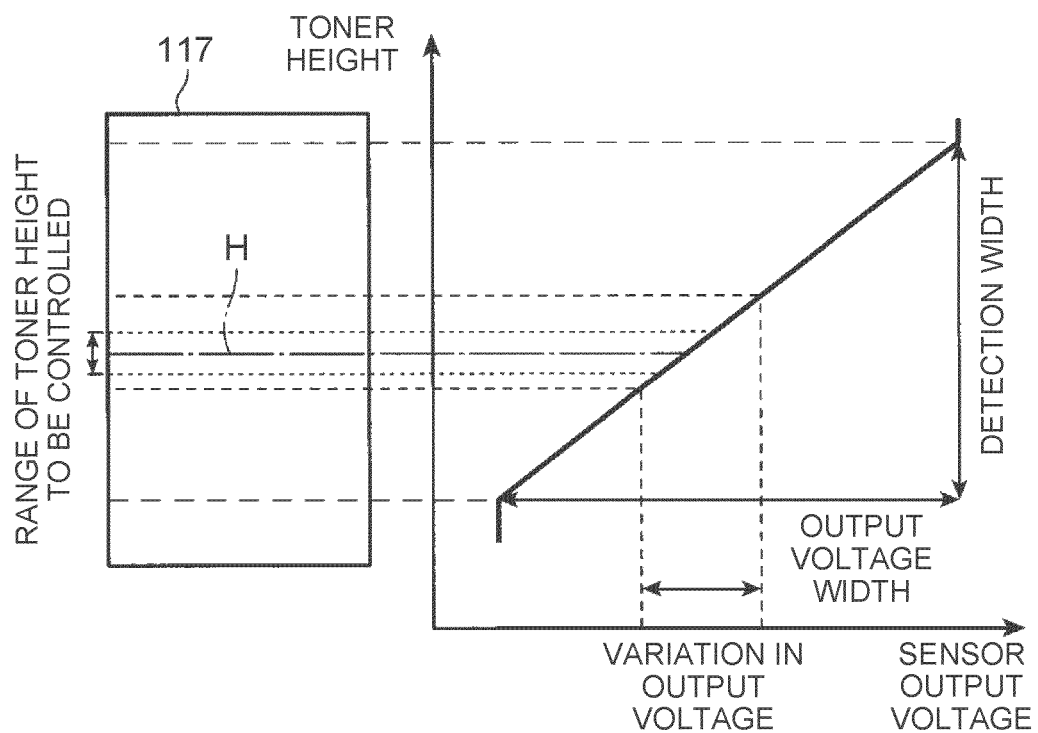
FIG. 14 is a graph showing a relation between an output voltage of a differential transformer type magnetic sensor according to a comparative example and a height of toner contained in a development part

In the image forming apparatus 1 according to the present embodiment, it is possible to improve precision with which a small change in quantity of the toner contained in the development part 117 is detected. This will be described using FIGS. 13 and 14. FIG. 13 is a graph showing a relation between the output voltage of the differential transformer type magnetic sensor 3 provided for the image forming apparatus 1 according to the present embodiment and the height of the toner contained in the development part 117. FIG. 14 is a graph showing a relation between the output voltage of the differential transformer type magnetic sensor according to a comparative example and the height of the toner contained in the development part 117. The magnetic sensor according to the comparative example is different from that of the present embodiment shown in FIG. 12, and is mounted on the outer lateral face of the cabinet of the development part 117 with the first direction D1 that is the direction of the short side of each of the first drive coil 4, the first differential coil 6, the second drive coil 5, and the second differential coil 7 set to be horizontal and with the second direction D2 that is the direction of the long side of each of these coils set to be vertical.

The horizontal axis of the graph shown in FIGS. 13 and 14 denotes the output voltage of the sensor, and the vertical axis denotes the height of the toner. The height of the toner is, in other words, the residual quantity of the toner contained in the development part 117.

The reference height H of the toner, a range of the height of the toner which is to be controlled, an output voltage width of the magnetic sensor, and a variation in output voltage of the magnetic sensor are the same in both the present embodiment shown in FIG. 13 and the comparative example shown in FIG. 14. The output voltage width is a width between the minimum value and the maximum value of the output voltage. The variation in output voltage occurs due to temperature of a place at which the magnetic sensor is disposed.

In the present embodiment, the height of the toner is detected with the first direction D1 that is the direction of the short side of each of the first drive coil 4, the first differential coil 6, the second drive coil 5, and the second differential coil 7 set to be vertical. In the comparative example, the height of the toner is detected with the second direction D2 that is the direction of the long side of each of these coils set to be vertical. For this reason, with regard to a detectable width of the height of the toner, the present embodiment is narrower than the comparative example. Since the output voltage width of the present embodiment is equal to that of the comparative example, a change in output voltage of the sensor with respect to a change in height of the toner is greater in the present embodiment than in the comparative example.

As described above, according to the present embodiment, with respect to the small change in the height of the toner contained in the development part 117, the change in the output voltage of the sensor can be increased. For this reason, it is possible to improve the precision with which the small change in the height of the toner contained in the development part 117, i.e. the small change in the quantity of the toner contained in the development part 117, is detected.

As mentioned above, in the comparative example, the change in the output voltage of the sensor with respect to the change in the height of the toner is small. For this reason, in the comparative example, the variation in the output voltage of the sensor cannot be absorbed, and as shown in FIG. 14, the height of the toner is out of the range of the height of the toner which is to be controlled. On the other hand, in the present embodiment, the change in the output voltage of the sensor with respect to the change in the height of the toner is great. For this reason, in the present embodiment, the variation in the output voltage of the sensor can be absorbed, and as shown in FIG. 13, the height of the toner can be within the range of the height of the toner which is to be controlled.

The foregoing description has been made of the case in which the drive coil of the differential transformer type sensor includes the first drive coil 4 disposed on the first surface 31 of the board 21 and the second drive coil 5 disposed on the second surface 41 of the board 21, the first drive coil 4 is magnetically coupled with the first differential coil 6, and the second drive coil 5 is magnetically connected to the second differential coil 7. However, the content presented in the present disclosure is not necessarily limited to this case. The drive coil of the differential transformer type sensor may be made up of one planar coil. In this case, for example, a configuration in which, with respect to a board having two insulating layers, the first differential coil is disposed on the top surface of the first insulating layer, the drive coil is disposed between the bottom surface of the first insulating layer and the top surface of the second insulating layer, and the second differential coil is disposed on the bottom surface of the second insulating layer is taken into consideration. Even in this configuration, similar to the differential transformer type sensor according to the present embodiment, if the dimension of the first direction of each of the drive coil, the first differential coil, and the second differential coil is smaller than that of the second direction, it is possible to improve the precision with which the small change in the quantity of the toner contained in the development part is detected.

Other effects of the present embodiment will be described. According to the present embodiment, as shown in FIG. 12, the differential transformer type magnetic sensor 3 is disposed on the development part 117 so that the central portion of each of the first drive coil 4, the first differential coil 6, the second drive coil 5, and the second differential coil 7 is located at the position of the reference height H of the toner contained in the development part 117.

For this reason, in the vicinity of the reference height H of the toner contained in the development part 117, the change in the output voltage of the sensor can be increased with respect to the small change in the height of the toner. Accordingly, while the residual quantity of the toner contained in the development part 117 is controlled to the reference height H, the residual quantity of the toner in the development part 117 can be controlled with high precision when an electrostatic latent image is developed to a toner image.

Further, as shown in FIG. 10A and FIG. 10B, in the present embodiment, the connection patterns 8*a*, 8*b*, 8*c*, and 8*d*, each of which serves as a part of the second differential coil 7, are disposed on the first surface 31. For this reason, a balance between the lengths of the coils (i.e., the first drive coil 4 and the first differential coil 6) disposed on the first surface 31 and the lengths of the coils (i.e., the second drive coil 5 and the second differential coil 7) disposed on the second surface 41 collapses. The collapse of the balance causes a reduction in measurement precision of the sensor. As such, it is preferable that lengths of the connection patterns 8*a*, 8*b*, 8*c*, and 8*d* be short.

According to the present embodiment, the connection patterns 8*a*, 8*b*, 8*c*, and 8*d* extend in the first direction D1 and are disposed on the first surface 31. The dimension of the first direction D1 of each of the first drive coil 4, the first differential coil 6, the second drive coil 5, and the second differential coil 7 is smaller than that of the second direction D2. Accordingly, in comparison with when the connection patterns 8*a*, 8*b*, 8*c*, and 8*d* extend in the second direction D2 and are disposed on the first surface 31, according to the present embodiment, since the lengths of the connection patterns 8*a*, 8*b*, 8*c*, and 8*d* can be reduced, it is possible to suppress the reduction in the measurement precision of the sensor.

Furthermore, the present embodiment has the following effects. In the present embodiment, as shown in FIG. 4, since the wire rod 4*a* constituting the first drive coil 4 and the wire rod 6*a* constituting the first differential coil 6 are alternately disposed, it is possible to increase magnetic coupling of these coils. Further, as shown in FIG. 5, since the wire rod 5*a* constituting the second drive coil 5 and the wire rod 7*a* constituting the second differential coil 7 are alternately disposed, it is possible to increase magnetic coupling of these coils.

Since the second drive coil 5 and the second differential coil 7 are wound in opposite directions, crossing of the wire rod 5*a* constituting the second drive coil 5 and the wire rod 7*a* constituting the second differential coil 7 is inevitable. When the second drive coil 5 and the second differential coil 7 come into contact with each other, a short circuit occurs between these coils. Thus, in the present embodiment, the wire rod 5*a* constituting the second drive coil 5 and the wire rod 7*a* constituting the second differential coil 7 are grade-separated using the connection patterns 8*a* to 8*d* and the third connecting members (not shown) formed in the board 21 in a penetrated state. Thereby, while the wire rod 5*a* constituting the second drive coil 5 and the wire rod 7*a* constituting the second differential coil 7 are crossed, the contact between the second drive coil 5 and the second differential coil 7 is prevented.

In the present embodiment, the first drive coil 4 and the first differential coil 6 are disposed on the first surface 31 of the board 21, and the second drive coil 5 and the second differential coil 7 are disposed on the second surface 41 which is located on the opposite side of the first surface 31. In this way, since the first drive coil 4, the first differential coil 6, the second drive coil 5, and the second differential coil 7 are disposed on a piece of board, miniaturization of the magnetic sensor 3 is achieved.

According to the present embodiment, the magnetic coupling of the first drive coil 4 and the first differential coil 6 and the magnetic coupling of the second drive coil 5 and the second differential coil 7 can be increased, and the magnetic sensor 3 can be miniaturized. Further, since the first drive coil 4, the first differential coil 6, the second drive coil 5, and the second differential coil 7 are disposed on a one-layered board rather than a multi-layered board, it is possible to reduce a cost of the magnetic sensor.

Conventionally, there has been a demand to detect the small change in the quantity of the detection target (toner) using the differential transformer type magnetic sensor. When the residual quantity of the toner contained in the development part is little, a quantity of the toner supplied to the electrostatic latent image is insufficient, and an image becomes blurred. On the other hand, when the residual quantity of the toner contained in the development part is great, the toner is insufficiently charged when agitated and charged. Both of these contribute to a reduction in image quality.

Thus, a reference quantity of the toner contained in the development part (in other words, a reference height of the toner contained in the development part) is controlled to a preset setting value using the magnetic sensor. To form a high-quality image, an allowable range of the change in the quantity of the toner is narrow. As such, it is necessary to detect the small change in the quantity of the toner contained in the development part.

With regard to the above problems, in the embodiment according to the mode for carrying out the present disclosure, since the dimension of the first direction of each of the drive coil, the first differential coil, and the second differential coil is smaller than that of the second direction, the change in the output voltage of the sensor can be increased with respect to the small change in the height of the toner contained in the development part. For this reason, it is possible to improve the precision with which the small change in the quantity of the toner contained in the development part is detected.

In the present embodiment, as shown in FIG. 10A and FIG. 10B, the connection patterns 8*a* to 8*d* are grade-separated by formation into a part of the second differential coil 7. However, the connection patterns 8*a* to 8*d* may be grade-separated by formation into a part of the second drive coil 5.

In the present embodiment, as shown in FIG. 6, the first drive coil 4 and the first differential coil 6 are formed on the same layer, and the second drive coil 5 and the second differential coil 7 are formed on the same layer. However, each of these coils may be formed on a separate layer. Further, the first drive coil 4 and the second drive coil 5 may be used as one drive coil, and each of the first differential coil 6, the drive coil, and the second differential coil 7 may be formed on a separate layer.

In the present embodiment, the differential transformer type magnetic sensor 3 has been described as a sensor that detects the residual quantity of the toner in the development part 117 of the image forming apparatus 1 as an example. However, the use of the differential transformer type magnetic sensor according to the present disclosure is not limited to the detection of the residual quantity of the toner in the development part 117.

The photosensitive drum 113 and the exposure part 115 of FIG. 1 function as a latent image forming part that forms the latent image indicated by the image data. In the present embodiment, the description has been made of the type in which the electrostatic latent image indicated by the image data is formed on the photosensitive drum 113, and this electrostatic latent image is developed by the toner. However, the type of the development is not limited to such a type. A type in which the electrostatic latent image indicated by the image data is formed on the paper, and this electrostatic latent image is developed by the toner may be used, and a type in which the toner is supplied to a magnetic latent image indicated by the image data, and the magnetic latent image is developed may be used.

Various modifications and alterations of this disclosure will be apparent to those skilled in the art without departing from the scope and spirit of this disclosure, and it should be understood that this disclosure is not limited to the illustrative embodiments set forth herein.

What is claimed is:

1. A differential transformer type magnetic sensor comprising:
    a board;
    a drive coil that includes a polygonal planar coil in which a dimension of a first direction which is one of longitudinal and transverse dimensions is smaller than that of a second direction which is the other of the longitudinal and transverse dimensions, and that is disposed on the board;
    a first differential coil that includes a planar coil along which induced current flows due to magnetic flux generated as drive current flows along the drive coil and which has the same shape as the drive coil, and that is disposed on the board; and
    a second differential coil that includes a planar coil along which induced current flows due to magnetic flux generated as drive current flows along the drive coil and which has the same shape as the drive coil, and that is disposed on the board,
    wherein the first differential coil and the second differential coil are electrically connected so that a direction of the induced current flowing along the first differential coil and a direction of the induced current flowing along the second differential coil are opposite to each other;
    when viewed from a thickness direction of the board, an array region of the drive coil, an array region of the first differential coil, and an array region of the second differential coil overlap;
    the board includes a first surface and a second surface located on the opposite side of the first surface;
    the drive coil includes a first drive coil that is disposed on the first surface and a second drive coil that is wound in the opposite direction of the first drive coil when viewed from a side of the first surface and is disposed on the second surface;
    the first differential coil is wound in the same direction as the first drive coil, and the first differential coil and the first drive coil are disposed on the first surface so that a wire rod constituting the first differential coil and a wire rod constituting the first drive coil are alternately disposed;
    the second differential coil is wound in the opposite direction of the second drive coil, and the second differential coil and the second drive coil are disposed on the second surface so that a wire rod constituting the second differential coil and a wire rod constituting the second drive coil are alternately disposed;
    the differential transformer type magnetic sensor includes:
        a first connecting member that is formed by penetrating the board and electrically connects one end of the first drive coil and one end of the second drive coil;
        a second connecting member that is formed by penetrating the board and electrically connects one end of the first differential coil and one end of the second differential coil;
        a third connecting member that is formed by penetrating the board; and
    connection patterns that are disposed on the first surface and are used as a part of the second drive coil or a part of the second differential coil; and
    the connection patterns grade-separate the wire rod constituting the second differential coil and the wire rod constituting the second drive coil by connecting the wire rod constituting the second drive coil or the wire rod constituting the second differential coil using the third connecting member.

2. The differential transformer type magnetic sensor according to claim 1, wherein the first drive coil, the second drive coil, the first differential coil, and the second differential coil have a rectangular shape in which a direction of a short side thereof is the first direction, and a direction of a long side thereof is the second direction.

3. The differential transformer type magnetic sensor according to claim 2, wherein the connection patterns extend in the first direction and are disposed on the first surface.

4. A image forming apparatus
    equipped with a differential transformer type magnetic sensor providing an output corresponding to a height of toner contained in a development part, the differential transformer type magnetic sensor comprising:
    a board;
    a drive coil that includes a planar coil in which a dimension of a first direction which is one of longitudinal and transverse dimensions is smaller than that of a second direction which is the other of the longitudinal and transverse dimensions, and that is disposed on the board;
    a first differential coil that includes a planar coil along which induced current flows due to magnetic flux generated as drive current flows along the drive coil and which has the same shape as the drive coil, and that is disposed on the board; and
    a second differential coil that includes a planar coil along which induced current flows due to magnetic flux generated as drive current flows along the drive coil and which has the same shape as the drive coil, and that is disposed on the board,
    wherein the first differential coil and the second differential coil are electrically connected so that a direction of the induced current flowing along the first differential coil and a direction of the induced current flowing along the second differential coil are opposite to each other;
        the differential transformer type magnetic sensor is disposed on a development part with the first direction set to be along a height direction of toner contained in a development part and with the second direction set to be perpendicular to the height direction;

the board includes a first surface and a second surface located on the opposite side of the first surface;

the drive coil includes a first drive coil that is disposed on the first surface and a second drive coil that is wound in the opposite direction of the first drive coil when viewed from a side of the first surface and is disposed on the second surface;

the first differential coil is wound in the same direction as the first drive coil, and the first differential coil and the first drive coil are disposed on the first surface so that a wire rod constituting the first differential coil and a wire rod constituting the first drive coil are alternately disposed;

the second differential coil is wound in the opposite direction of the second drive coil, and the second differential coil and the second drive coil are disposed on the second surface so that a wire rod constituting the second differential coil and a wire rod constituting the second drive coil are alternately disposed;

when viewed from a thickness direction of the board, an array region of the first drive coil, an array region of the first differential coil, an array region of the second drive coil, and an array region of the second differential coil overlap;

the differential transformer type magnetic sensor includes:

a first connecting member that is formed by penetrating the board and electrically connects one end of the first drive coil and one end of the second drive coil;

a second connecting member that is formed by penetrating the board and electrically connects one end of the first differential coil and one end of the second differential coil;

a third connecting member that is formed by penetrating the board; and connection patterns that are disposed on the first surface and are used as a part of the second drive coil or a part of the second differential coil; and the connection patterns grade-separate the wire rod constituting the second differential coil and the wire rod constituting the second drive coil by connecting the wire rod constituting the second drive coil or the wire rod constituting the second differential coil using the third connecting member.

5. The image forming apparatus according to claim 4, wherein the first drive coil, the second drive coil, the first differential coil, and the second differential coil have a rectangular shape in which a direction of a short side thereof is the first direction, and a direction of a long side thereof is the second direction.

6. The image forming apparatus according to claim 5, wherein the connection patterns extend in the first direction and are disposed on the first surface.

7. The image forming apparatus according to claim 4, wherein the differential transformer type magnetic sensor is disposed on the development part so that a central portion of each of the drive coil, the first differential coil, and the second differential coil is located at a position of a reference height of the toner contained in the development part.

* * * * *